United States Patent [19]
Adams et al.

[11] Patent Number: 5,382,575
[45] Date of Patent: Jan. 17, 1995

[54] (N-PYRIDINIUMPHENYL)-CARBAPENEMS

[75] Inventors: Alan D. Adams, Piscataway; Frank DiNinno, Old Bridge; James V. Heck, Scotch Plains, all of N.J.

[73] Assignee: Merck & Co., Inc., Rahway, N.J.

[21] Appl. No.: 957,974

[22] Filed: Oct. 7, 1992

Related U.S. Application Data

[63] Continuation of Ser. No. 777,947, Oct. 17, 1991, abandoned.

[51] Int. Cl.$^6$ ............... C07D 487/00; A01N 43/00; A61K 31/395
[52] U.S. Cl. ..................... 514/210; 540/302
[58] Field of Search .................. 540/302; 514/210

[56] References Cited

U.S. PATENT DOCUMENTS

| | | |
|---|---|---|
| 4,260,627 | 4/1981 | Christensen et al. |
| 4,269,772 | 5/1981 | Melillo et al. |
| 4,309,438 | 1/1982 | Christensen et al. |
| 4,350,631 | 9/1982 | Christensen et al. |
| 4,383,946 | 5/1983 | Christensen et al. |
| 4,414,155 | 11/1983 | Liu et al. |
| 4,465,632 | 8/1984 | Christensen et al. |
| 4,479,947 | 10/1984 | Christensen. |
| 4,543,257 | 9/1985 | Cama et al. |
| 4,729,993 | 3/1988 | Christensen et al. |
| 4,775,669 | 10/1988 | Cama et al. |
| 4,962,101 | 10/1990 | Dininno et al. |
| 4,978,659 | 12/1990 | Dininno et al. |
| 5,004,739 | 4/1991 | Dininno et al. |
| 5,004,740 | 4/1991 | Dininno et al. |
| 5,006,519 | 4/1991 | Dininno et al. |
| 5,011,832 | 4/1991 | Dininno et al. |
| 5,025,006 | 6/1991 | Dininno et al. |
| 5,025,007 | 6/1991 | Dininno et al. |
| 5,025,008 | 6/1991 | Dininno et al. |
| 5,032,587 | 7/1991 | Dininno et al. |
| 5,034,384 | 7/1991 | Dininno et al. |
| 5,034,385 | 7/1991 | Dininno et al. |
| 5,037,820 | 8/1991 | Dininno et al. |

FOREIGN PATENT DOCUMENTS

| | | |
|---|---|---|
| 0185315 | 8/1988 | European Pat. Off. |
| 0277743 | 8/1988 | European Pat. Off. |

OTHER PUBLICATIONS

Wentrup, C. et al. J. Am. Chem. Soc. 102:6161–6163 (1980).
Melillo, D. G., et al. Tet. Let. 21:2783–2786 (1980).
De Vries, J. G., et al. Heterocycles 23(8):1915–1919 (1985).
Fuentes, L. M., et al., J. Am. Chem. Soc. 108:4675–4676 (1986).
Cama, et al. Tetrahedron 39:2531 (1983).
Guthikonda, et al. J. Med. Chem. 30:871 (1987).
Bryce, et al. Bull. Soc. Chem. FR. 1986 (6) 930–2.

*Primary Examiner*—Johann Richter
*Assistant Examiner*—Rebecca Cook
*Attorney, Agent, or Firm*—Richard C. Billups; Mark R. Daniel; Joseph F. DiPrima

[57] ABSTRACT

Carbapenems of the formula

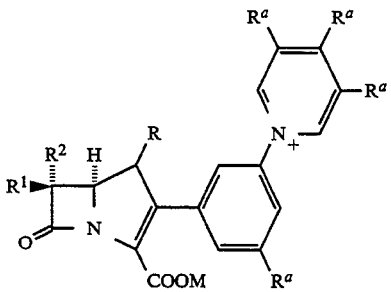

are useful antibacterial agents.

17 Claims, No Drawings

(N-PYRIDINIUMPHENYL)-CARBAPENEMS

This is a continuation of application Ser. No. 07/777,947, filed Oct. 17, 1991 now abandoned.

BACKGROUND OF THE INVENTION

The present invention relates to antibacterial agents of the carbapenem class, in which the 2-position sidechain is characterized by a N-pyridiniumphenyl moiety, substituted by various cationic and neutral substituents, as described in more detail further below.

Thienamycin was an early carbapenem antibacterial agent having a broad spectrum; it has the following formula:

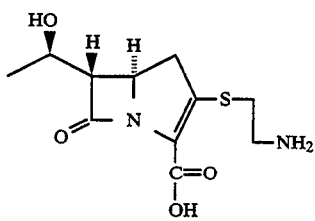

Later, N-formimidoyl thienamycin was discovered; it has the formula:

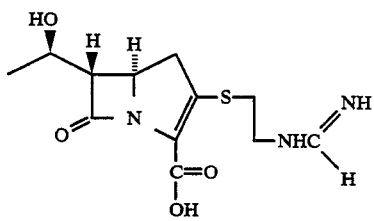

The 2-(N-pyridiniumphenyl)-carbapenems of the present invention are not only of interest for a broad antibacterial spectrum such as that of thienamycin or N-formimidoyl thienamycin. Rather, their spectrum of activity of special interest is to gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

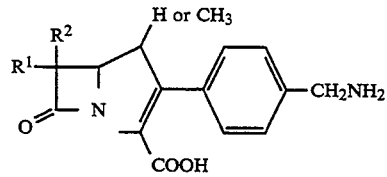

However, there is no description or suggestion of a N-pyridiniumphenyl 2-substituent such as characterizes the compounds of the present invention, nor is there any suggestion of the surprisingly better anti-MRSA/MRCNS activity of the compounds of the present invention.

U.S. Pat. No. 4,978,659 describes a particular class of compounds of the formula:

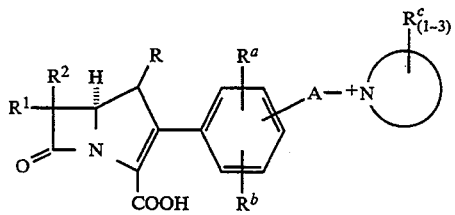

but this limited teaching in no way suggests the totally different compounds of the present invention, nor their surprisingly better anti-MRSA/MRCNS activity.

SUMMARY OF INVENTION

The present invention provides novel carbapenem compounds of the formula:

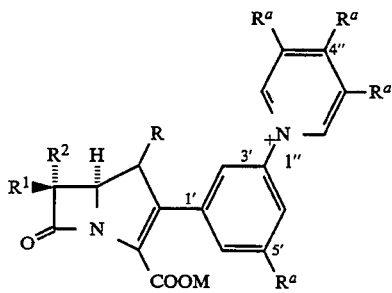

wherein:
R is H or $CH_3$;
$R^1$ and $R^2$ are independently H, $CH_3-$, $CH_3CH_2-$, $(CH_3)_2CH-$, $HOCH_2-$, $CH_3CH(OH)-$, $(CH_3)_2C(OH)-$, $FCH_2CH(OH)-$, $F_2CHCH(OH)-$, $F_3CCH(OH)-$, $CH_3CH(F)-$, $CH_3CF_2-$, or $(CH_3)_2C(F)-$;
$R^a$ are independently selected from the group consisting of hydrogen and the radicals set out below:
a) a trifluoromethyl group: $-CF_3$;
b) a halogen atom: $-Br$, $-Cl$, $-F$, or $-I$;
c) $C_1$-$C_4$ alkoxy radical: $-OC_{1-4}$ alkyl, wherein the alkyl is optionally mono-substituted by $R^q$, where $R^q$ is a member selected from the group consisting of $-OH$, $-OCH_3$, $-CN$, $-C(O)NH_2$, $-OC(O)NH_2$, CHO, $-OC(O)N(CH_3)_2$, $-SO_2NH_2$, $-SO_2N(CH_3)_2$, $-SOCH_3$, $-SO_2CH_3$, $-F$, $-CF_3$, $-COOM^a$ (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and —$SO_3M^b$ (where $M^b$ is hydrogen or an alkali metal);

d) a hydroxy group: —OH;

e) a carbonyloxy radical: —O(C=O)$R^s$, where $R^s$ is $C_{1-4}$ alkyl or phenyl, each of which is optionally mono-substituted by $R^q$ as defined above or tri-substituted with —F;

f) a carbamoyloxy radical: —O(C=O)N($R^y$)$R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S—, —S(O)— or —S(O)$_2$— to form a ring (where the ring is optionally mono-substituted with $R^q$ as defined above);

g) a sulfur radical: —S(O)$_n$—$R^s$ where n=0-2, and $R^s$ is defined above;

h) a sulfamoyl group: —SO$_2$N($R^y$)$R^z$ where $R^y$ and $R^z$ are as defined above;

i) azido: N$_3$ j) a formamido group: —N($R^t$)(C=O)H, where $R^t$ is H or $C_{1-4}$ alkyl, and the alkyl thereof is optionally mono-substituted by $R^q$ as defined above;

k) a ($C_1$-$C_4$ alkyl)carbonylamino radical: —N($R^t$)(C=O)$C_{1-4}$ alkyl, where $R^t$ is as defined above, and the alkyl group is also optionally mono-substituted by $R^q$ as defined above;

l) a ($C_1$-$C_4$ alkoxy) carbonylamino radical: —N($R^t$)(C=O)O$C_{1-4}$ alkyl, where $R^t$ is as defined above, and the alkyl group is also optionally mono-substituted by $R^q$ as defined above;

m) a ureido group: —N($R^t$)(C=O)N($R^y$)$R^z$ where $R^t$, $R^y$ and $R^z$ are as defined above;

n) a sulfonamido group. —N($R^t$)SO$_2R^s$, where $R^s$ and $R^t$ are as defined above;

o) a cyano group: —CN;

p) a formyl or acetalized formyl radical: —(C=O)H or —CH(OCH$_3$)$_2$;

q) ($C_1$-$C_4$ alkyl)carbonyl radical wherein the carbonyl is acetalized: —C(OCH$_3$)$_2C_{1-4}$ alkyl, where the alkyl is optionally mono-substituted by $R^q$ as defined above;

r) carbonyl radical: —(C=O)$R^s$, where $R^s$ is as defined above;

s) a hydroximinomethyl radical in which the oxygen or carbon atom is optionally substituted by a $C_1$-$C_4$ alkyl group: —(C=NO$R^z$)$R^y$ where $R^y$ and $R^z$ are as defined above, except they may not be joined together to form a ring;

t) a ($C_1$-$C_4$ alkoxy)carbonyl radical: —(C=O)O$C_{1-4}$ alkyl, where the alkyl is optionally mono-substituted by $R^q$ as defined above;

u) a carbamoyl radical: —(C=O)N($R^y$)$R^z$ where $R^y$ and $R^z$ are as defined above;

v) an N-hydroxycarbamoyl or N($C_1$-$C_4$ alkoxy)-carbamoyl radical in which the nitrogen atom may be additionally substituted by a $C_1$-$C_4$ alkyl group: —(C=O)—N(O$R^y$)$R^z$ where $R^y$ and $R^z$ are as defined above, except they may not be joined together to form a ring;

w) a thiocarbamoyl group: —(C=S)N($R^y$)($R^z$) where $R^y$ and $R^z$ are as defined above;

x) carboxyl: —COO$M^b$, where $M^b$ is as defined above;

y) thiocyanate: —SCN;

z) trifluoromethylthio: —SCF$_3$;

aa) tetrazolyl, where the point of attachment is the carbon atom of the tetrazole ring and one of the nitrogen atoms is mono-substituted by hydrogen, an alkali metal or a $C_1$-$C_4$ alkyl optionally substituted by $R^q$ as defined above;

ab) an anionic function selected from the group consisting of: phosphono [P=O(O$M^b$)$_2$]; alkylphosphono {P=O(O$M^b$)—[O($C_1$-$C_4$ alkyl)]}; alkylphosphinyl [P=O(O$M^b$)—($C_1$-$C_4$alkyl)]; phosphoramido [P=O(O$M^b$)N($R^y$)$R^z$ and P=O-(O$M^b$)NH$R^x$]; sulfino (SO$_2M^b$); sulfo (SO$_3M^b$); acylsulfonamides selected from the structures CON$M^b$SO$_2R^x$, CON$M^b$SO$_2$N($R^y$)$R^z$, SO$_2$N$M^b$CON($R^y$)$R^z$; and SO$_2$N$M^b$CN, where $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;

ac) $C_5$-$C_7$ cycloalkyl group in which one of the carbon atoms in the ring is replaced by a heteroatom selected from O, S, NH or N($C_1$-$C_4$ alkyl) and in which one additional carbon atom may be replaced by NH or N($C_1$-$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2$-$C_4$ alkenyl radical, optionally mono-substituted by one of the substituents a) to ac) above and phenyl which is optionally substituted by $R^q$ as defined above;

ae) $C_2$-$C_4$ alkynyl radical, optionally mono-substituted by one of the substituents a) to ac) above;

af) $C_1$-$C_4$ alkyl radical;

ag) $C_1$-$C_4$ alkyl mono-substituted by one of the substituents a)–ac) above;

ah) a 2-oxazolidinonyl moiety in which the point of attachment is the nitrogen atom of the oxazolidinone ring, the ring oxygen atom is optionally replaced by a heteroatom selected from —S— and N$R^t$ (where $R^t$ is as defined above) and one of the saturated carbon atoms of the oxazolidinone ring is optionally mono-substituted by one of the substituents a) to ag) above; and M is selected from:

i) hydrogen;

ii) a pharmaceutically acceptable esterifying group or removable carboxyl protecting group;

iii) an alkali metal or other pharmaceutically acceptable cation; or iv) absent, leaving COO−.

The present invention also provides novel carbapenem intermediates of the formula:

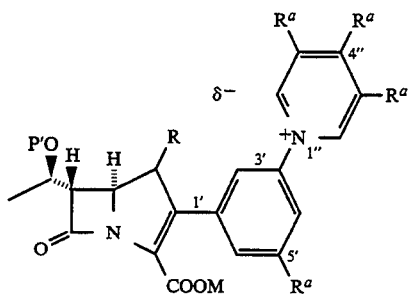

wherein:

R is H or CH$_3$;

R$^a$ is defined above, with the proviso that R$^a$ additionally includes Me$_3$Sn, that R$^q$ additionally includes OP' where P' is defined below, that M$^a$ and M$^b$ of R$^q$ both include M and that the Type d) hydroxy substituent additionally may be protected hydroxy, OP';

δ— is a counter ion;

P' is a removable protecting group for hydroxy or hydrogen; and

M is a removable protecting group for carboxy.

Preferred intermediates have the formula:

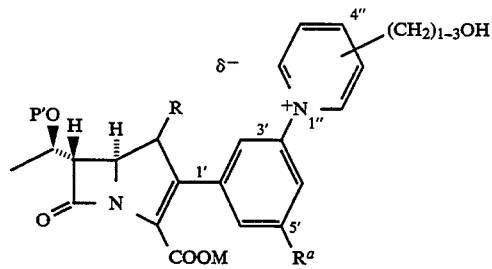

wherein

R is H or CH$_3$;

δ— is a counterion;

P' is a removable protecting group for hydroxy or hydrogen;

M is a removable protecting group for carboxy;

R$^a$ is selected from the group consisting of H, OP', Cl, Br, I, SCH$_3$, CN, CHO, SOCH$_3$, SO$_2$CH$_3$, CO$_2$M, CH$_2$OP', Sn(Me)$_3$ or CONH$_2$; and with the proviso that the —(CH$_2$)$_{1-3}$—OH substituent is in the 3"- or 4"-position of the N-pyridiniumphenyl and may be optionally absent.

DETAILED DESCRIPTION OF THE INVENTION

The manufacture of compounds of Formula I may be carried out in a three-stage synthesis scheme followed by a final step which allows for the removal of any protecting groups. The objective of a first synthetic stage is to produce a base N-pyridiniumphenyl compound which may be converted to the two-position substituent of the carbapenem of Formula I. The objective of a second synthetic stage is to attach the base N-pyridiniumphenyl to the carbapenem. Finally, the objective of a third synthetic stage is to introduce the desired R$^a$. This third synthetic stage may be performed at any point according to the nature of the various R$^a$.

Flow Sheets A and B demonstrate a suggested first stage synthesis. Flow Sheet C demonstrates a second stage synthesis in which the products of Flow Sheets A and B may be utilized. The third synthesis varies according to the selected R$^a$. Flow Sheet D demonstrates a variation on the above suggested scheme.

The suggested first synthesis of Flow Sheet A can generally be described as a Zincke exchange reaction. In this reaction, a Zincke reagent of the formula:

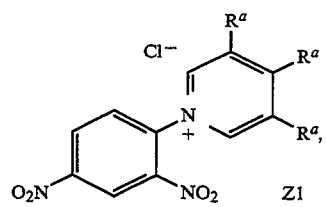

wherein R$^a$ is defined above or a precursor substituent therefor, is employed to produce intermediate C1. The Zincke reagent may be prepared by reacting 1-chloro-2,4-dinitrobenzene with a pyridine compound of the formula:

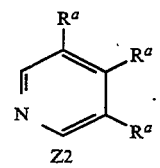

Of course certain R$^a$ are compatible with this reaction and others may require the use of a protecting group or a suitable precursor substituent. Suitable substituted pyridines Z2 and their manufacture are well known to persons skilled in the art.

The Zincke reagent Z1 is employed to produce the base N-pyridiniumphenyl C1 in a Zincke reaction according to Flow Sheet A as follows:

FLOW SHEET A

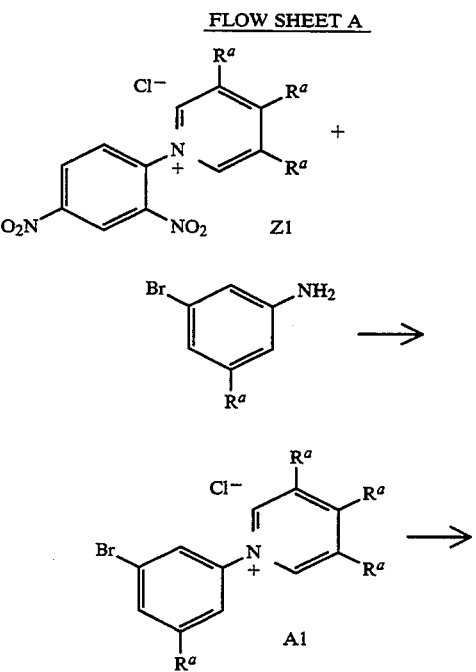

-continued
FLOW SHEET A

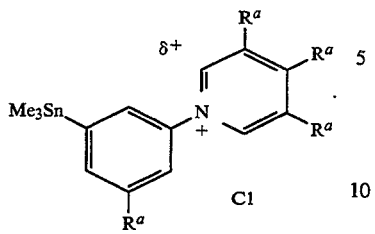

Again, $R^a$ is defined above or a precursor substituent therefor. This reaction of Flow Sheet A is generally carried out in the presence of a suitable base, such as triethylamine or sodium methoxide, in an appropriate organic solvent, e.g. methanol or dioxane, at a temperature ranging from about 20° to 120° C. and for a time of from about 30 minutes to 2 hours. Clearly, suitable $R^a$ for this Zincke reaction, may change as compared to suitable $R^a$ for formation of the Zincke reagent. Modification might be required in a protecting group, in a precursor substituent or in a $R^a$ which was stable in the formation of the reagent. The Zincke reaction is well known in the art and is further described in Zincke, et al., Annalen, 1904, 333, 296; Lettré, Annalen, 1953, 579, 123; Keijzer, et al., Heterocycles, Vol. 16, No. 10, 1981, 1687.

Following the Zinke reaction, of Flow Sheet A, N-pyridiniumphenyl A1 is converted to the trimethylstannyl-N-pyridiniumphenyl C1. This might be accomplished by reacting N-pyridiniumphenyl A1 with hexamethylditin in the presence of a palladium(O) catalyst such as tetrakis(triphenylphosphine)palladium(O) in an inert solvent such as toluene at from 25° to 110° C. for from 0.25–24 hours to provide the stannane C1.

In a preferred modification of Flow Sheet A, the aryl stannane C1 may be produced directly by first stannylating the 3-position bromine of aniline in Flow Sheet A. The stannylation may be accomplished using hexamethylditin with a palladium catalyst. In this modification, $R^a$ may conveniently be bromine and the hexamethylditin stoichiometry controlled to produce 3-trimethylstannyl-5-bromoaniline.

The suggested first synthesis of Flow Sheet B, in broad terms, employs an arylium salt with either a fluoroborate or fluorophosphate anion to produce N-pyridiniumphenyl C1. As shown in Flow Sheet B, two routes might be taken with this approach.

FLOW SHEET B

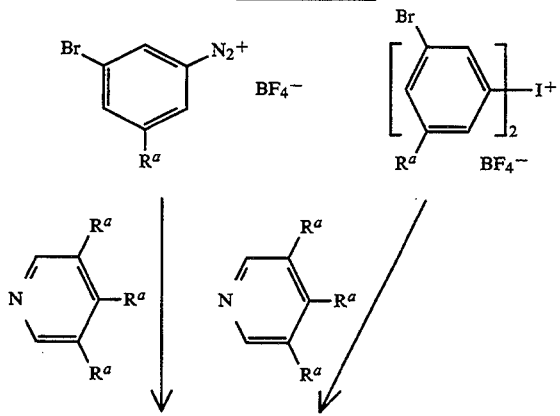

-continued
FLOW SHEET B

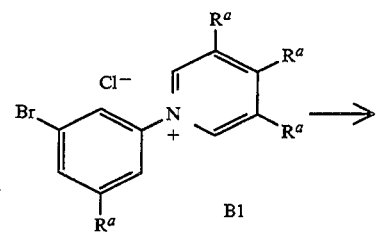

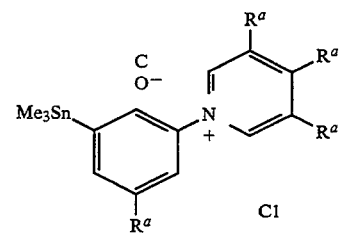

In one route of Flow Sheet B, a diphenyliodonium salt is used to arylate an appropriately substituted pyridine to produce B1. In the alternative, an isolated diazonium salt might be similarly used to yield B1. B1 may be subsequently, stannylated to C1 by the method given above to stannylate A1.

The starting materials for Flow Sheet B are within the skill of the art. The diazonium salt might be prepared from otherwise suitably substituted m-bromoaniline. The m-bromoaniline might be diazotized by first treating with chlorosulfonic acid to produce a soluble sulfamic acid and subsequently with $HNO_2$ and HCl to produce, in generic terms, $ArNN^+Cl^-$, a diazonium chloride salt. The tetrafluoroborate or hexafluoro phosphate salt might be precipitated by the addition of sodium tetrafluoroborate or sodium hexafluorophosphate. The diphenyliodonium salt might be produced using m-bromoaniline which is, again, converted to the diazonium salt with chlorine. The chloride salt, however, in this case is reacted with CuI in a Sandmeyer reaction to produce 1-iodo-3-bromophenyl, which may be reacted with further diazonium salt to produce a diphenyliodonium chloride. This is converted to the tetrafluoroborate or hexafluorophosphate salt by reaction with sodium tetrafluoroborate or sodium hexafluorophosphate.

The object compounds of Flow Sheets A and B form the nucleus of the 2-position substitution of the carbapenem compounds taught herein. As such it is shown to be $R^a$ substituted. However, it is immediately clear to those skilled in the art that certain $R^a$ listed above, if substituted on intermediates to C1 would not survive or permit the synthesis to compound C1. Thus, where a certain $R^a$ is desired and this $R^a$ is not compatible with the synthesis scheme to produce C1 then a compatible precursor substituent may be employed through the synthesis.

The identity of the precursor substituent employed is not crucial so long as it does not interfere with the synthesis to C1 and so long as it may be thereafter converted to a more desireable substituent. Preferred precursor substituents for $R^a$ are methyl, hydroxymethyl and protected hydroxymethyl.

Thus, as to the $R^a$ substituent on compound C1, it may be an $R^a$ with or without protecting groups stable to the conditions of producing compound C1, and stable to the conditions of subsequently adding C1, to the carbapenem. Alternatively, it may be a stable precursor substituent which is stable to the conditions of making C1, which is optionally stable to the conditions of adding C1, to the carbapenem and which is convertible to a desired $R^a$ or to another precursor substituent.

As stated above, the second stage synthesis is to attach the base N-pyridiniumphenyl C1 to the 2-position of the carbapenem. This synthesis involves a palladium catalyzed cross-coupling reaction between a carbapenem triflate and a suitably substituted arylstannane, a process which is described in U.S. patent application Ser. No. 650,011 filed Feb. 4, 1991, hereby incorporated by reference. Referring to Flow Sheet C, the 2-oxocarbapenam is reacted with a suitable trifluoromethanesulfonyl source, such as trifluoromethanesulfonic anhydride, in the presence of an organic nitrogen base, such as triethylamine, diisopropylamine and the like, in polar aprotic solvent, such as tetrahydrofuran or methylene chloride. Optionally, an organic nitrogen base, such as triethylamine and the like, is then added to the reaction solution followed immediately by a silylating agent, such as trimethylsilyl trifluoromethanesulfonate to provide intermediate C2. An aprotic polar coordinating solvent, such as DMF, 1-methyl-2-pyrrolidinone and the like, is optionally added. This is followed by the addition of a palladium compound, such as tris(dibenzylidene-acetone)dipalladium-chloroform, palladium acetate and the like, optionally, a suitably substituted phenylphosphine, such as tris(4-methoxyphenyl)phosphine, tris(2,4,6-trimethoxyphenyl)phosphine and the like, and the stannane C3. A halide source, such as lithium chloride, zinc chloride or tetraalkylammonium chlorides and the like, is added and the reaction solution is allowed to warm and is stirred at a suitable temperature, such as 0° to 50° C. for from a few minutes to 48 hours. The carbapenem C4 is obtained by conventional isolation/purification methodology known in the art.

Generally speaking, the milder conditions of the synthesis shown in Flow Sheet C allow for a wider range of functional groups $R^a$ to be present than the synthesis illustrated in Flow Sheet D to follow. However, in certain cases it is advantageous for the $R^a$ substituent(s) of the stannane C1 to be introduced in a protected or precursory form. Final elaboration of $R^a$ from a precursor substituent, e.g. iodide or hydroxymethyl, may be accomplished on carbapenem intermediate C4. Removal of hydroxyl and carboxyl protecting groups then provides the final compound of Formula I. Such final elaboration and deprotection is described in further detail below.

It is clear that in each instance where a charged N-pyridiniumphenyl is shown or discussed, there is by necessity a counterion $\delta^-$. Thus, intermediates Z1, A1, B1 and the preferred intermediates described above, as well as the active compounds, may have a counterion to the charged N-pyridiniumphenyl. The identity of the counterion will, initially at least, depend on the leaving group employed in the attachment of the pyridinium. Herein, for example, $\delta^-$ might be chlorine from the preparation of the Zincke reagent or a fluoroborate or fluorophosphate anion as suggested in Flow Sheet B. Of course, the counterion is easily replaced with various counterions which have no connection to the counterion formation. For example, chloride is not a highly reactive leaving group, but as $Cl^-$ it can readily serve as a suitable replacement counterion.

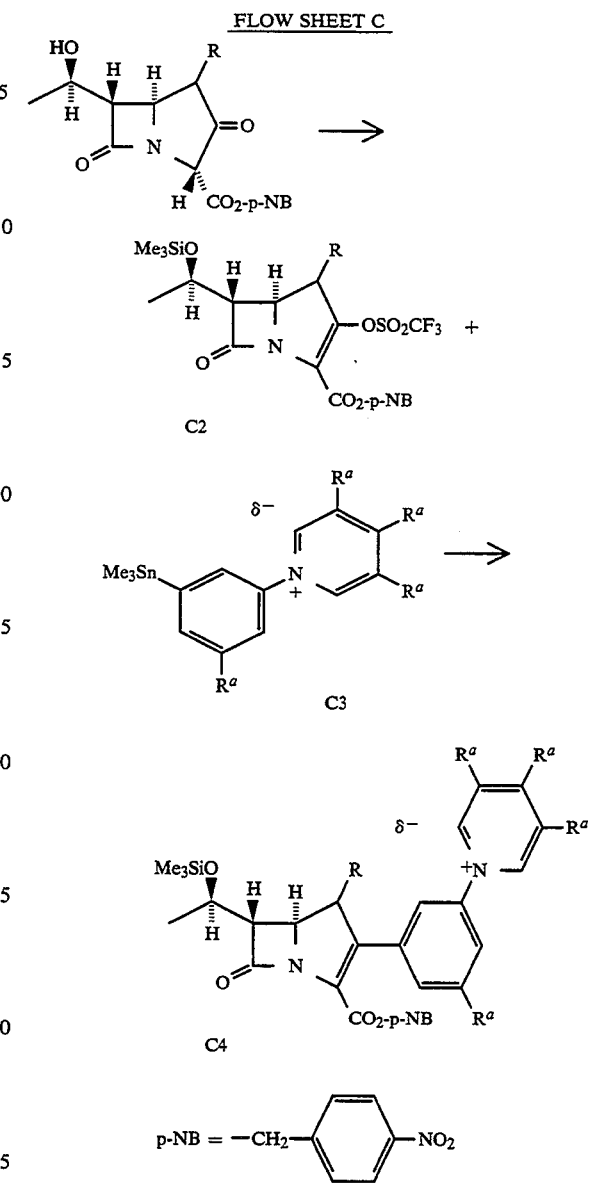

It is known generally where aryl moieties are attached to the 2-position of carbapenem that a Grignard reaction might be employed to attach a Grignard reagent equivalent to C1 to an azetidinone of the type D2. However, it is believed herein that a Grignard reaction is incompatible with a N-pyridiniumphenyl compound due to the presence of the quaternized nitrogen. Thus, if the Grignard reaction is to prove useful to produce carbapenems herein, it is necessary to assemble the 2-position substituent in such a fashion that the Grignard reaction is performed prior to forming the N-pyridinium moiety. Thus, with stable $R^a$ or suitable precursor substituents therefor, an appropriate phenyl compound might be added to azetidin-2-one D2 in a Grignard reaction as shown in Flow Sheet D. An appropriate phenyl might be one containing a stable $R^a$ in addition to, AMIN, a protected amine or stable precursor substituent therefor that can be converted to amine following the Grignard reaction. The amine might subsequently be useful in a Zincke reaction to add pyridinium either prior to closing the ring at D3 or after ring closure at D4. The Grignard reaction requires that D1, for example, be converted to a Grignard reagent by reaction with magnesium and 1,2-dibromoethane in THF from 20° C. to 60° C. and subsequently contacting D1 as a Grignard reagent with D2 in THF at from −70° C. to about 20° C. to produce azetidin-2-one D3. Alternatively, D1 may be reacted with t-butyl-lithium, n-butyllithium, or the like in THF at from −78° to −50° C. followed by the addition of magnesium bromide to produce the same Grignard reagent. $R^i$ of D2 is in practice pyrid-2-yl but may clearly be a variety of substituents including aromatic and heteroaromatic substituents. Further $R^i$ might be for example phenyl, 2-pyrimidinyl or 2-thiazolyl.

Azetidin-2-one D3 is an intermediate that might be ring closed to a carbapenem. It is on this intermediate that $R^a$ or precursor substituents might be modified where such modification is incompatible with the carbapenem nucleus.

Compound D3 might be ring closed to carbapenem D4 by refluxing in xylene with a trace of p-hydroquinone for about 1 to 2 hours in an inert atmosphere. It is on this intermediate that final elaboration of $R^a$ from a precursor substituent, e.g. hydroxymethyl, might be accomplished. Removal of the carboxyl and hydroxyl protecting groups then provides the final compound of Formula I. Such final elaboration and deprotection is described in further detail below.

FLOW SHEET D

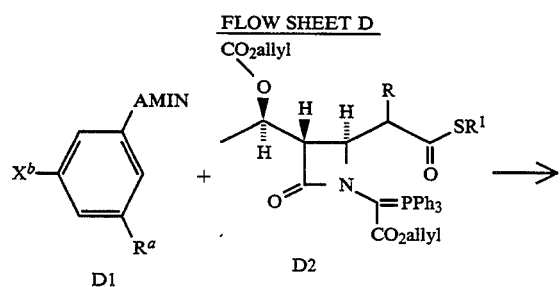

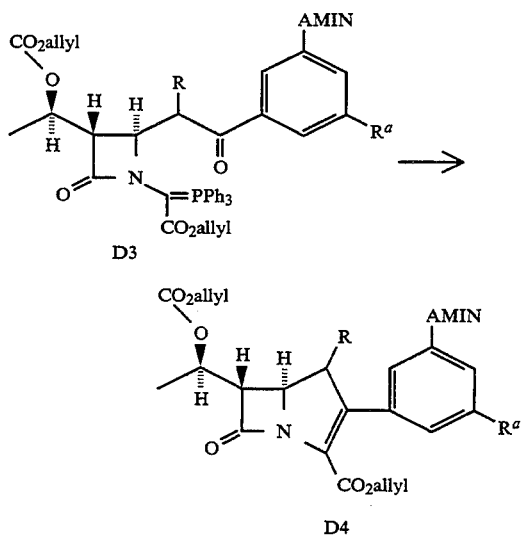

Azetidin-2-one E2, a pyridyl-thioester, is a well known compound in the production of carbapenems. Diverse synthetic schemes useful to make E2 may be imagined by the skilled artisan. Particularly useful to the instant invention is a synthetic scheme set out further in Flow Sheet D below in which the symbol R is as defined above. The steps for preparing intermediate E2 are analogous to the procedures described, for example, in U.S. Pat. Nos. 4,260,627 and 4,543,257; L. D. Cama et al. *Tetrahedron* 39, 2531 (1983); R. N. Guthikonda et al. *J. Med. Chem.*, 30, 871 (1987).

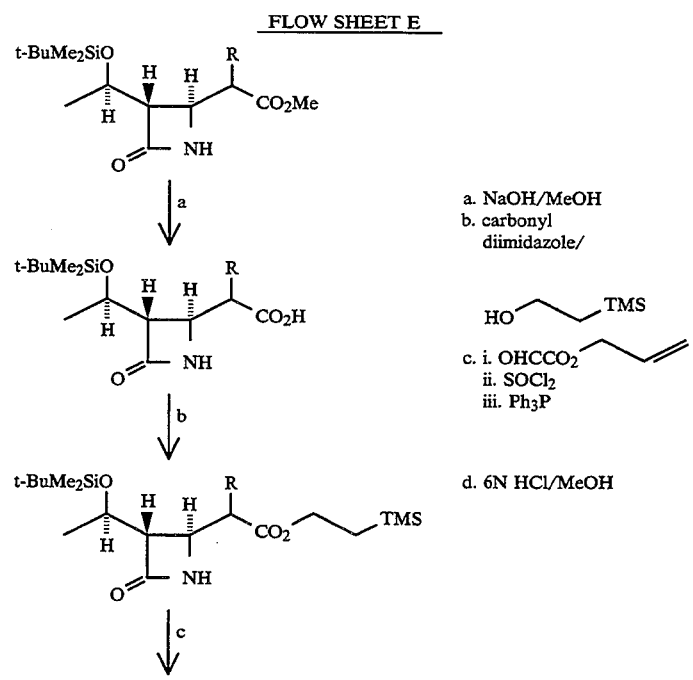

FLOW SHEET E

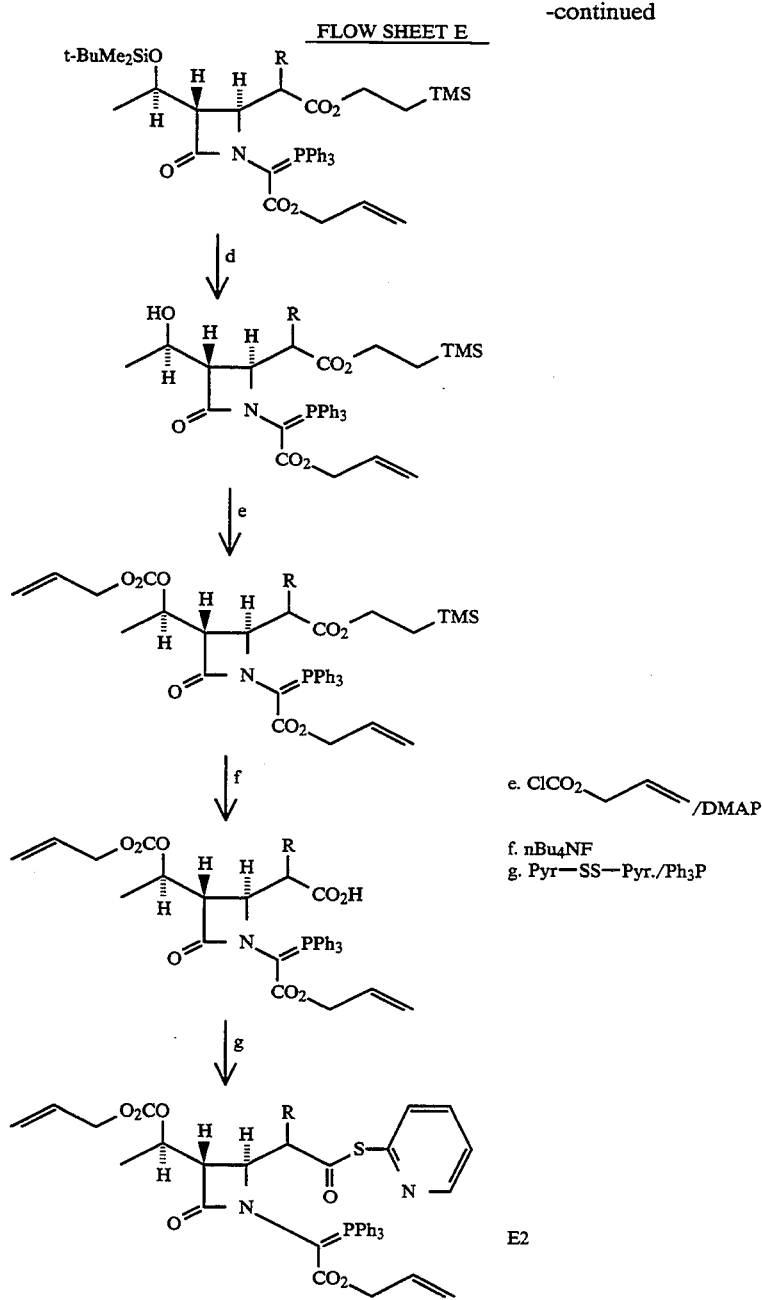

e. ClCO₂―/―/DMAP
f. nBu₄NF
g. Pyr—SS—Pyr./Ph₃P

The steps for preparing the 2-oxocarbapenam intermediate of Flow Sheet C are well known in the art and are explained in ample detail by D. G. Melillo et al., *Tetrahedron Lett.,* 1980, 21, 2783, T. Salzmann etal., *J. Am. Chem. Soc.,* 1980, 102, 6161, and L. M. Fuentes, I. Shinkai, and T. N. Salzmann, *J. Am. Chem. Soc.,* 1986, 108, 4675. The syntheses are also disclosed in U.S. Pat. No. 4,269,772, U.S. Pat. No. 4,350,631, U.S. Pat. No. 4,383,946 and U.S. Pat. No. 4,414,155 all assigned to Merck and Company, Inc. and hereby incorporated by reference.

The general synthesis description depicted above in the Flow Sheets shows a protected. 1-hydroxyethyl substitution on the 6-position of the carbapenem. In certain situations, it may not be necessary to protect this substituent as shown. It may be the case that an unprotected hydroxy substituent will survive the coupling of Flow Sheet C and subsequent manipulations of $R^a$. Persons skilled in the art can determine those instances in which the protecting group is necessary.

After final deprotection, a 1-hydroxyethyl substituent is obtained, which is preferred in most cases. However, it has been found that with certain 2-side-chain selections, the ultimate balance of favorable properties in the overall molecule may be enhanced by selection of the 6-(1-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles,* 1985, 23, 1915; BE 900 718 A (Sandoz) and Japanese Patent Pub. No. 6-0163-882-A (Sanraku Ocean).

In preferred compounds of Formula I, $R^1$ is hydrogen. More preferably, $R^1$ is hydrogen and $R^2$ is (R)—$CH_3CH(OH)$— or (R)—$CH_3CH(F)$—. In the most preferred case, $R^1$ is hydrogen and $R^2$ is (R)—$CH_3CH(OH)$—. While R=H is usually preferred, there are instances in which R=$CH_3$ may provide improved chemical stability, water solubility, or pharmacokinetic behavior. The substituent R=$CH_3$ may be of either configuration, i.e., the α or β-stereoisomer. Additionally, in preferred compounds, at least $R^a$ in the 5'-position of the N-pyridiniumphenyl is other than hydrogen. In the most preferred compounds, in total, one or two $R^a$ substituents are other than hydrogen.

Suitable $R^a$ are described above in the text associated with Formula I. Among preferred $R^a$ are $C_{1-4}$ alkyl mono-substituted with hydroxy, such as, hydroxymethyl or 3-hydroxypropyl; formyl; alkoxycarbonyl, such as, —$COOCH_3$; carbamoyl, such as, —$CONH_2$; hydroxoximinomethyl, such as, —CH=NOH; iodo; or cyano.

In regard to this preferred substitution, a hydroxymethyl or 3-hydroxypropyl might be substituted on ring Z1, the starting materials for Flow Sheet B or the aniline of Flow Sheet A by standard procedures. These substituents might then be appropriately protected for the syntheses to follow.

The preferred formyl substitution on the N-pyridiniumphenyl may be obtained on C4 from the hydroxymethyl substitution, in the case of $R^a$, by a Swern oxidation. For example, C4 is oxidized in methylene chloride at from $-70°$ C. to room temperature employing oxalyl chloride-dimethyl sulfoxide followed by triethylamine as the active agent. Obviously, the position of the resultant formyl substitution will depend upon the position of the hydroxymethyl substitution on C4.

The preferred —CH=NOH substitution on the N-pyridiniumphenyl might be conveniently obtained from the formyl substitution just described. This is accomplished simply by exposing the formyl substituted compound to hydroxylamine in an appropriate solvent at room temperature.

The preferred iodo may be obtained from a trimethylstannyl substituted C1, the production of which is exemplified in Example 1, as compound 4. The 5'-trimethylstannyl substituent may be converted of iodo after coupling C1 to carbapenem by dissolving in chloroform and treating with a slight excess of iodine.

The preferred cyano substitution on the N-pyridiniumphenyl might be obtained from the aniline of Flow Sheet A in which $R^a$ is bromine or from Z2 where $R^a$ is bromine. The bromine substituted compound is reacted with copper (I) cyanide in N-methylpyrrolid-2-one (3 hours at 180° C.).

The —$COOCH_3$ substitution on the N-pyridiniumphenyl might be obtained from a methyl substituted A1, B3, C1, or C4. The methyl substituent might be oxidized with chromium trioxide or $^nBu_4NMnO_4$ to form carboxy.

The preferred carbamoyl substitution on the N-pyridiniumphenyl, might be obtained from C4 with carboxylic acid substitution as described immediately above. This carboxylic acid substituent is converted to the carboxamide group, —$CONH_2$, by sequentially contacting with 1-ethyl-3-(3-dimethylaminopropyl)carbodiimide hydrochloride, 1-hydroxybenzotriazole, and ammonia in an organic solvent at room temperature. Substituted amides might of course be obtained by replacing ammonia with the corresponding substituted amine. Alternatively, the carbamoyl substitution might be obtained by hydrolysis of the nitrile of the cyano substituent described above.

In the preparation methods described above, the carboxyl group at the 3-position and, optionally, the hydroxyl group at the 8-position of the carbapenem remain blocked by protecting groups until the penultimate product is prepared. Suitable hydroxyl protecting groups, P', are silyl groups such as trialkylsilyl, aryl(alkyl)alkoxysilyl, alkoxydiarylsilyl and diarylalkylsilyl and carbonate groups such as alkyloxycarbonyl, substituted alkyloxycarbonyl, benzyloxycarbonyl, substituted benzyloxycarbonyl , allyloxycarbonyl and substituted allyloxycarbonyl. The preferred protecting groups, in addition to or including those shown in the schemes, are t-butylmethoxyphenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Suitable carboxyl protecting groups, M, in addition to or including those shown in the schemes are described herein below.

Deblocking may be carried out in a conventional manner. For compounds prepared according to Flow Sheet D, deprotection might be carried out in a palladium catalyzed reaction in a solution containing potassium 2-ethylhexanoate and 2-ethylhexanoic acid or, alternatively, another suitable nucleophile such as pyrrolidine. Alternatively, for those prepared via Flow Sheet C, deprotection is conducted sequentially. Thus, compound C4 is exposed initially, when hydroxy at the 8-position is protected, to aqueous acidic conditions, acetic acid or dilute HCl or the like, in an organic solvent such as tetrahydrofuran at 0° C. to ambient temperature for from a few minutes to several hours. The resulting desilylated carbapenem may be isolated by conventional techniques, but is more conveniently taken into the final deprotection process. Thus, addition of an inorganic base such as $NaHCO_3$ or $KHCO_3$ and a catalyst, such as, 10% Pd/C or 5% $Rh/Al_2O_3$ followed by hydrogenation provides for the removal of the p-nitrobenzyl protecting group and the formation of the final compound of Formula I.

With reference to the above definitions, "alkyl" means a straight or branched chain aliphatic hydrocarbon radical.

The term "heteroatom" means N, S, or O, selected on an independent basis.

The term "heteroaryl" has been defined herein, in relation to the $R^x$ group, to have a specific and limited meaning, being only monocyclic. It is required that the monocyclic heteroaryl have at least one nitrogen atom, and optionally at most only one additional oxygen or sulfur heteroatom may be present. Heteroaryls of this type are pyrrole and pyridine (1N); and oxazole, thiazole or oxazine (1N 1O or 1S). While additional nitrogen atoms may be present together with the first nitrogen and oxygen or sulfur, giving, e.g., a thiadiazole (2N's+1S), the preferred heteroaryls are those where only nitrogen heteroatoms are present when there is more than one. Typical of these are pyrazole, imidazole, pyrimidine and pyrazine (2N's) and triazine (3N's).

The heteroaryl group of $R^x$ is always optionally mono-substituted by $R^q$, defined above, and substitution can be on one of the carbon atoms or one of the heteroatoms, although in the latter case certain substitutent choices may not be appropriate.

Listed in Tables I and II are specific compounds of the instant invention:

TABLE I

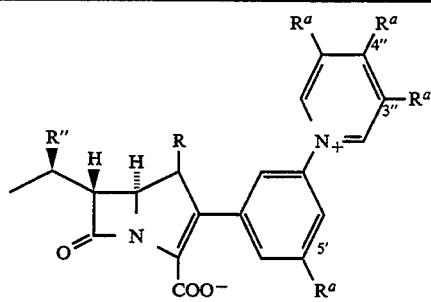

where R″ is F or OH, R is H or Me and $R^a$ is:

| # | $R^a$ | $R^a$ position |
|---|---|---|
| 1 | —H | — |
| 2 | —OCH$_3$ | 5′ |
| 3 | —OCH$_2$CO$_2$CH$_3$ | 5′ |
| 4 | —OCH$_2$CH$_2$OH | 5′ |
| 5 | —CF$_3$ | 5′ |
| 6 | —F | 5′ |
| 7 | —Cl | 5′ |
| 8 | —Br | 5′ |
| 9 | —I | 5′ |
| 10 | —OH | 5′ |
| 11 | —OCOCH$_3$ | 5′ |
| 12 | —OCONH$_2$ | 5′ |
| 13 | —SCH$_3$ | 5′ |
| 14 | —SOCH$_3$ | 5′ |
| 15 | —SO$_2$CH$_3$ | 5′ |
| 16 | —SCH$_2$CH$_2$OH | 5′ |
| 17 | —SOCH$_2$CH$_2$OH | 5′ |
| 18 | —SCH$_2$CONH$_2$ | 5′ |
| 19 | —SO$_2$NH$_2$ | 5′ |
| 20 | —SO$_2$N(CH$_3$)$_2$ | 5′ |
| 21 | —NHCHO | 5′ |
| 22 | —NHCOCH$_3$ | 5′ |
| 23 | —NHCO$_2$CH$_3$ | 5′ |
| 24 | —NHSO$_2$CH$_3$ | 5′ |
| 25 | —CN | 5′ |
| 26 | —CHO | 5′ |
| 27 | —COCH$_3$ | 5′ |
| 28 | —COCH$_2$OH | 5′ |
| 29 | —CH=NOH | 5′ |
| 30 | —CH=NOCH$_3$ | 5′ |
| 31 | —CH=NOCH$_2$CO$_2$CH$_3$ | 5′ |
| 32 | —CH=NOCMe$_2$CO$_2$CH$_3$ | 5′ |
| 33 | —CH=NOCMe$_2$CONH$_2$ | 5′ |
| 34 | —CO$_2$CH$_2$CH$_2$OH | 5′ |
| 35 | —CONH$_2$ | 5′ |
| 36 | —CONHCH$_3$ | 5′ |
| 37 | —CON(CH$_3$)$_2$ | 5′ |
| 38 | —CONHCH$_2$CN | 5′ |
| 39 | —CONHCH$_2$CONH$_2$ | 5′ |
| 40 | —CONHCH$_2$CO$_2$CH$_3$ | 5′ |
| 41 | —CONHOH | 5′ |
| 42 | —CONHOCH$_3$ | 5′ |
| 43 | -tetrazolyl | 5′ |
| 44 | —CO$_2$CH$_3$ | 5′ |
| 45 | —SCF$_3$ | 5′ |
| 46 | —CONHSO$_2$Ph | 5′ |
| 47 | —CONHSO$_2$NH$_2$ | 5′ |
| 48 | —SO$_2$CF$_3$ | 5′ |
| 49 | —SO$_2$NHCN | 5′ |
| 50 | —SO$_2$NHCONH$_2$ | 5′ |
| 51 | —CH=CHCN | 5′ |
| 52 | —CH=CHCONH$_2$ | 5′ |
| 53 | —CH=CHCO$_2$CH$_3$ | 5′ |
| 54 | —C≡C—CONH$_2$ | 5′ |
| 55 | —C≡C—CN | 5′ |
| 56 | —CH$_2$OH | 5′ |
| 57 | —CH$_2$N$_3$ | 5′ |
| 58 | —CH$_2$CO$_2$CH$_3$ | 5′ |
| 59 | —SO$_2$CH$_2$CH$_2$OH | 5′ |
| 60 | —CH$_2$I | 5′ |

TABLE I-continued

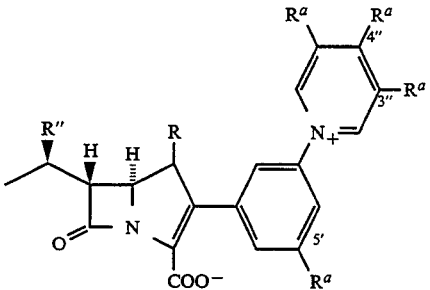

where R″ is F or OH, R is H or Me and $R^a$ is:

| # | $R^a$ | $R^a$ position |
|---|---|---|
| 61 | —CONH$_2$ | 3″ |
| 62 | —CONH$_2$ | 4″ |
| 63 | —CN | 3″ |
| 64 | —CN | 4″ |
| 65 | —CHO | 3″ |
| 66 | —CHO | 4″ |
| 67 | —CH$_2$OH | 3″ |
| 68 | —CH$_2$OH | 4″ |
| 69 | —Br | 3″ |
| 70 | —Br | 4″ |
| 71 | —I | 3″ |
| 72 | —I | 4″ |
| 73 | —SO$_2$CH$_3$ | 3″ |
| 74 | —SO$_2$CH$_3$ | 4″ |
| 75 | —S(O)CH$_3$ | 3″ |
| 76 | —S(O)CH$_3$ | 4″ |
| 77 | —SCH$_3$ | 3″ |
| 78 | —SCH$_3$ | 4″ |
| 79 | —COOCH$_3$ | 3″ |
| 80 | —COOCH$_3$ | 4″ |
| 81 | —CH=NOH | 3″ |
| 82 | —CH=NOH | 4″ |

TABLE II

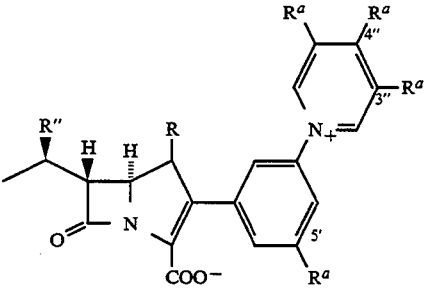

where R″ is F or OH, R is H or Me and $R^a$ is:

| # | $R^a$ | |
|---|---|---|
| 1 | 3″-CH$_2$OH | 5′-Br |
| 2 | 4″-CH$_2$OH | 5′-Br |
| 3 | 3″-CH$_2$OH | 5′-CN |
| 4 | 4″-CH$_2$OH | 5′-CN |
| 5 | 3″-CH$_2$OH | 5′-S(O)$_2$Me |
| 6 | 4″-CH$_2$OH | 5′-S(O)$_2$Me |
| 7 | 3″-CH$_2$OH | 5′-I |
| 8 | 4″-CH$_2$OH | 5′-I |
| 9 | 3″-CHO | 5′-Br |
| 10 | 4″-CHO | 5′-Br |
| 11 | 3″-CHO | 5′-CN |
| 12 | 4″-CHO | 5′-CN |
| 13 | 3″-CHO | 5′-S(O)$_2$Me |
| 14 | 4″-CHO | 5′-S(O)$_2$Me |
| 15 | 3″-CHO | 5′-I |
| 16 | 4″-CHO | 5′-I |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Broadly, such ester protecting groups include alkyl, substituted alkyl, benzyl, substituted benzyl, aryl, substituted aryl, allyl, substituted allyl and triorganosilyl. Examples of specific such ester protecting groups include benzhydryl, p-nitrobenzyl, 2-naphthylmethyl, allyl, 2-chloroallyl, benzyl, t-butyl, 2,2,2-trichloroethyl, t-butyldimethylsilyl, t-butyldiphenylsilyl, trimethylsilyl, 2-(trimethyl)silylethyl, phenacyl, p-methoxybenzyl, acetonyl, o-nitrobenzyl and 4-pyridylmethyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of, means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5–50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5-25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

EXAMPLE 1

3-trimethylstannyl-5-bromoaniline 1, and 1,5-bis trimethylstannylaniline 2.

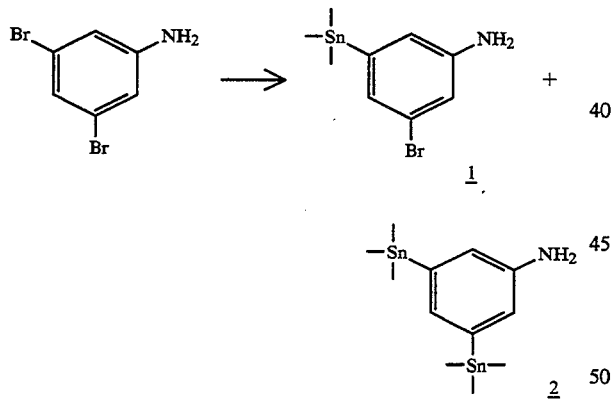

The stannanes 1 and 2 were prepared by dissolving the dibromoaniline (4 g, 16 mmol) in toluene (125 mL) with (Ph$_3$P)$_4$Pd (1.84 g, 1.6 mmol) and (Ph$_3$)P (0.42 g, 1.6 mmol). Hexamethylditin (4.0 mL, 19 mmol) was added, and the mixture degassed i. vac, and purged with N$_2$. The mixture was brought to reflux, and monitored by TLC for consumption of the dibromide. When SM was consumed (~¾HR) the reaction mixture was cooled and poured into CH$_2$Cl$_2$ and sat'd. NH$_4$Cl aq. The aqueous phase was extracted with CH$_2$Cl$_2$ three times, and the combined organic phases washed two more times with NH$_4$Cl aq. The organic phases were dried over Na$_2$SO$_4$, filtered and reduced i. vac. A 41% yield of the mono stannane 1, and a 43% yield of the bis-stannane were obtained from 1.2 equivalents of hexamethylditin. The products were purified by chromatography on 50 weight equivalents of SiO$_2$ with 95:5 CCl$_4$ ethyl acetate as eluent.

1 mono-stannane
$^1$H NMR [200 MHz, CDCl$_3$] 6.96 (m, 1H), 6.79 (m, 1H), 6.71 (m, 1H), 3.8 (brd, 2H), 0.28 (m, 9H).

2 bis-stannane
$^1$NMR [200 MHz, CDCl$_3$] 6.98 (m, 1H), 6.8 (m, 2H), 3.6 (brd, 2H), 0.27 (m, 9H).

1-(3'-trimethylstannyl-5'-bromophenyl)pyridinium chloride 3

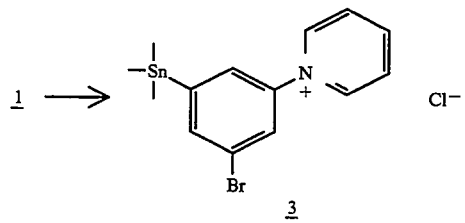

1-(2',4'-dinitrophenyl)pyridinium chloride (98 mg, 0.35 mmol) was dissolved in dioxane:water (4:1) with the stannane 1 (112 mg, 0.33 mmol) and diisopropylethylamine (58 ml, 0.33 mmol). The mixture was heated to 43° C. for three hours. The reaction mixture was reduced i. vac. and purified by chromatography on a Lobar RP-18 column with 30% CH$_3$CN in water as eluent. Recovery was typically poor (<50%).

$^1$H NMR [400 MHz, d6 Acetone] 9.72 (dd, 2H, 1.2,6.8 Hz), 8.95 (t, 1H, 7.9 Hz), 8.48 (t, 2H, 6.8 Hz), 8.32 (d,1H, 2 Hz), 8.27 (d, 1H, 2 Hz), 8.0 (m, 1H), 0.41 (m, 9H).

1-(3',5'-bis-trimethylstannylphenyl)pyridinium chloride 4

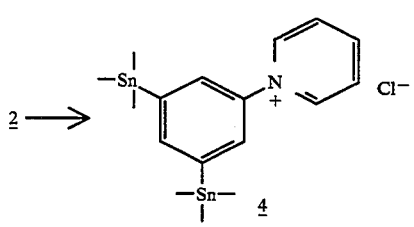

The bis-trimethyl stannane 4 was prepared and purified as for the mono-stannane 3. Recovery was similar.

$^1$H NMR [400 MHz, d6 Acetone] 9.68 (dd, 2H, 1.3,6.8 Hz), 8.92 (t, 1H, 7.8 Hz), 8.48 (dt, 2H, 1.0, 6.7 Hz), 8.13 (m, 2H), 8.0 (m, 1H) 0.366 (m, 9H).

p-Nitrobenzyl (5R,6S)-2-[3'-bromo-5'-[1'''-pyridinium]-phenyl]-6-[(1R)-1-hydroxyethyl]carbapen-2-em-3-carboxylate chloride. 5

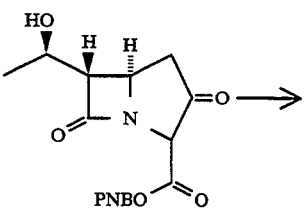

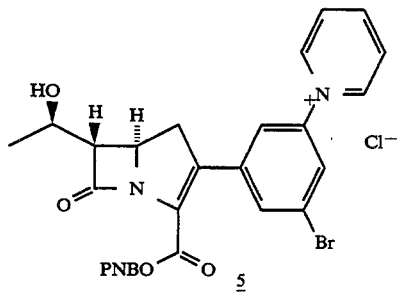

The bicyclic β-lactam (52 mg, 0.15 mmol) was dissolved in dry CH₂Cl₂ (2 mL) and cooled to −78° C. Diisopropylethylamine (29 μL, 0.16 mmol) was added, and the solution stirred 5 min. Neat trifluoromethanesulfonic anhydride (28 μL, 0.16 mmol) was added dropwise, and the resulting solution stirred 45 min at −78° C. to give a colorless suspension. Conversion to the enol triflate is monitored on E. Merck RP-18 analytical TLC plates with 98:2 toluene acetic acid as eluent. The stannane 3 was (65 mg, 0.15 mmol) dissolved in dry CH₂Cl₂ (3 mL) and added to the reaction mixture, followed by solid Pd₂DBA₃—CHCl₃ (15 mg 0.15 mmol) and solid Et₄NCl—(H₂O)ₓ, (25 mg, 0.15 mmol) (figured on 166 g/mol). The reaction mixture was warmed immediately to RT in a water bath. The solution was stirred at RT until the enol triflate was consumed (TLC 70:30 ethyl acetate on SiO₂, or system indicated above). The reaction was worked up by pouring into a mixture of brine and H₂O (1:1), and CH₂Cl₂ and acetone (1:1). The aqueous fraction was extracted several times with or CH₂Cl₂/CH₃CN. The organic extracts were dried over Na₂SO₄, filtered and reduced i. vac. The yield is given below for compound 6 after deprotection.

¹H NMR [400 MHz, d6 Acetone] 9.38 (dd, 2H, 1.4, 5.5 Hz), 8.95 (t, 1H, 7.8 Hz), 8.45 (dt, 2H, 1, 6.8 Hz), 8.2 (m, 2H), 8.14 (d, 1H, 1.5 Hz), 8.04 (t, 1H, 1.5 Hz), 7.73 (m, 1H), 7.68 (d, 2H, 9.1 Hz), 5.37 (ABq, 2H, Δν 58 Hz, J_AB 13.9 Hz), 4.41 (dt, 1H, 1.8, 3.0 Hz), 4.16 (m, 1H), 3.51 (AB of ABX system, 2H, Δν 111 Hz, J_AB 18.5, J_AX 10.3, J_BX 8.5 Hz), 3.47 (dd, 1H, 3.1, 6.3 Hz), 1.26 (d, 3H, 6.3 Hz).

(5R,6S)-2-[3′-bromo-5′-[1‴-pyridinium]phenyl]-6-[(1R)-1-hydroxyethyl]carbapen-2-em-3-carboxylate. 6

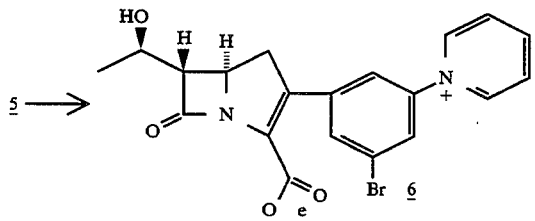

The p-nitrobenzyl ester 5 (assumed 0.15 mmol) was dissolved in 1:1 THF and ethanol. (2 mL each) Sodium bicarbonate (25 mg, 0.3 mmol) was added in H₂O, followed by 5% Rh on Al₂O₃ (14 mg). The reaction vessel was vacuum purged with H₂ three times and left to stir at RT. The consumption of the starting ester was monitored by TLC. Upon complete consumption of the ester, the mixture was filtered through a 0.45μ acrodisc, reduced i. vac., and residual water removed by lyophilization. The yield is 20% over two steps. Purification was by chromatography on a E. Merck Lobar RP-18 column with 9% CH₃CN in water as eluent.

¹H NMR [400 MHz, D₂O] 9.07 (dd, 2H, 6.8, 1.2 Hz), 8.76 (t, 1H, 7.2 Hz), 8.26 (t, 2H, 6.8 Hz), 7.88 (m, 2H), 7.69 (s, 1H), 4.36 (dt, 1H, 2.9, 10 Hz), 4.28 (p, 1H, 6.2 Hz), 3.58 (dd, 1H, 2.9, 5.9 Hz), 3.33 (AB of ABX system, 2H, Δν 118 Hz, J_AB 16.9, J_AX 9.97, J_BX 8.4 Hz), 1.32 (d, 3H, 6.5 Hz).

UV [H₂O, 0.1M MOPS pH=7] λmax=307 nm, ε=11775.

EXAMPLE 2

3-trimethylstannylaniline 7

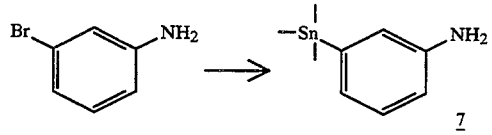

The stannane 7 was prepared as for compound 2. The yield was 52%. The product was purified by chromatography on SiO₂ with 95:5 CCl₄ ethyl acetate as eluent.

¹H NMR [200 MHz, CDCl₃] 7.16 (t, 1H, 7.3 Hz), 6.86 (m, 2H), 6.64 (m, 1H), 3.4 (brd, 2H), 0.27 (m, 9H).

1-(3′-trimethylstannylphenyl)pyridinium chloride 8

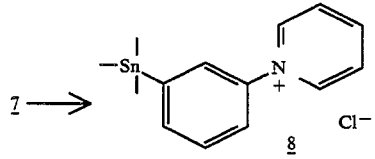

The stannane 8 was prepared and purified as for compound 3.

¹H NMR [400 MHz, CDCl₃] 9.35 (d, 2H, 5.6 Hz), 8.74 (t, 1H, 7.9 Hz), 8.51 (t, 2H, 6.8 Hz), 7.8 (m, 1H), 7.75 (m, 2H), 7.60 (t, 1H, 7.9 Hz), 0.36 (m, 9H).

p-Nitrobenzyl (5R,6S)-2-[3′-[1‴-pyridinium]phenyl]-6-[(1R)-1-hydroxyethyl]carbapen-2-em-3-carboxylate chloride. 9.

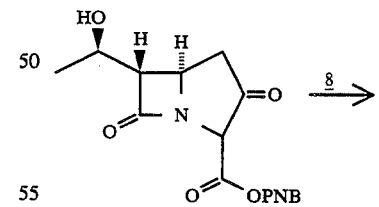

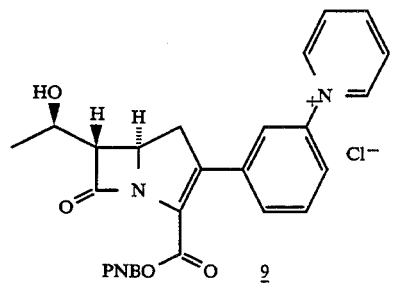

The coupling reaction of stannane 8 was as for compound 3. The yield is given below for compound 10 after deprotection.

¹H NMR [400 MHz, d6 Acetone] 9.36 (dd, 2H, 1.3, 6.8 Hz), 8.94 (t, 1H, 7.9 Hz), 8.45 (t, 2H, 6.8 Hz), 8.19 (d, 2H, 8.9 Hz), 7.7 (m, 4H), 7.66 (d, 2H, 8.9 Hz), 5.37 (ABq, 2H, Δν 56 Hz, $J_{AB}$ 14 Hz), 4.41 (m, 1H), 4.16 (p, 1H, 6.2 Hz), (AB of ABX system, 2H, Δν 109 Hz, $J_{AB}$ 18.5, $J_{AX}$ 10.2, $J_{BX}$ 8.5 Hz), 3.46 (m, 1H), 1.27 (d, 3H, 6.2 Hz).

(5R,6S)-2-[3'-[1''-pyridinium]phenyl]-6-[(1R)-1-hydroxyethyl]carbapen-2-em-3-carboxylate.10

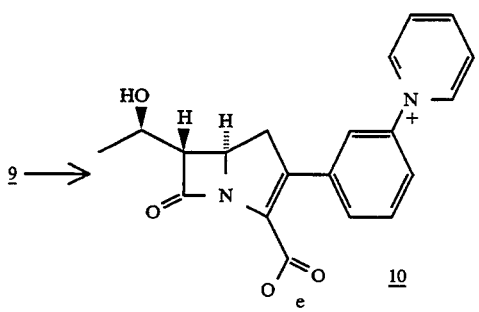

The carbapenem 9 was deprotected as for compound 5. The yield is 40% over two steps. Purification was by chromatography on a E. Merck Lobar RP-18 column with 14% CH₃CN in water as eluent.

¹H NMR [400 MHz, D₂O] 9.08 (dd, 2H, 1.2, 6.8 Hz), 8.73 (t, 1H, 7.9 Hz), 8.24 (t, 2H, 7.8 Hz), 7.67 (m, 4H), 4.34 (dt, 1H, 2.9, 9.9 Hz), 4.27 (p, 1H, 6.2 Hz), 3.55 (dd, 1H, 2.9, 6.0 Hz), 3.34 (AB of ABX system, 2H, Δν 131 Hz, $J_{AB}$ 17.1, $J_{AX}$ 9.9, $J_{BX}$ 8.5 Hz), 1.31 (d, 3H, 6.4 Hz).

UV [H₂O, 0.1M MOPS pH=7] λmax=305 nm, ε=12051, C=8.6.10-5

What is claimed is:

1. A compound of the formula:

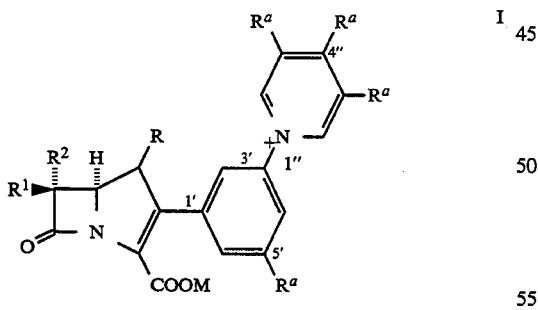

wherein:

R is H or CH₃;

R¹ and R² are independently H, CH₃—, CH₃CH₂—, (CH₃)₂CH—, HOCH₂—, CH₃CH(OH)—, (CH₃)₂C(OH)—, FCH₂CH(OH)—, F₂CHCH(OH)—, F₃CCH(OH)—, CH₃CH(F)—, CH₃CF₂—, or (CH₃)₂C(F)—;

Rᵃ are independently selected from the group consisting of hydrogen and the radicals set out below:
a) —CF₃;
b) a halogen atom selected from the group consisting of —, —Br, —Cl, —F, or —I;
c) —OC₁₋₄ alkyl, wherein the alkyl is optionally mono-substituted by R�q, where R�q is a member selected from the group consisting of —OH, —OCH₃, —CN, —C(O)NH₂, —OC(O)NH₂, CHO, —OC(O)N(CH₃)₂, —SO₂, NH₂, —SO₂N(CH₃)₂, —SOCH₃, —SO₂CH₃, —F, —CF₃, —COOMᵃ (where Mᵃ is hydrogen, alkali metal, methyl or phenyl), tetrazolyl (where the point of attachment is the carbon atom of the tetrazole ring and one of the nitrogen atoms is mono-substituted by Mᵃ as defined above) and —SO₃Mᵇ (where Mᵇ is hydrogen or an alkali metal);
d) —OH;
e) —O(C═O)Rˢ, where Rˢ is C₁₋₄ alkyl or phenyl, each of which is optionally mono-substituted by Rᑫ as defined above or tri-substituted with —F;

f) —O(C═O)N(Rʸ)Rᶻ where

Rʸ and Rᶻ are independently H, C1₁₋₄ alkyl (optionally mono-substituted by Rᑫ as defined above), together a 3- to 5-membered alkylidene radical to form a ring (optionally substituted with Rᑫ as defined above) or together a 2- to 4-membered alkylidene radical, interrupted by —O—, —S—, —S(O)— or —S(O)₂— to form a ring (where the ring is optionally mono-substituted with Rq as defined above);

g) —S(O)ₙ—Rˢ where n=0-2, and Rˢ is defined above;

h) —SO₂N(Rʸ)Rᶻ where Rʸ and Rᶻ are as defined above;

i) N₃ j) —N(Rᵗ)(C═O)H, where

Rᵗ is H or C₁₋₄ alkyl, and the alkyl thereof is optionally mono-substituted by Rᑫ as defined above;

k) —N(Rᵗ)(C═O)C₁₋₄ alkyl, where Rᵗ is as defined above, and the alkyl group is also optionally mono-substituted by Rᑫ as defined above;

l) —N(Rᵗ)(C═O)OC₁₋₄ alkyl, where Rᵗ is as defined above, and the alkyl group is optionally mono-substituted by Rᑫ as defined above;

m) —N(Rᵗ)(C═O)N(Rʸ)Rᶻ where Rᵗ, Rʸ and Rᶻ are as defined above;

n) —N(Rᵗ)SO₂Rˢ, where Rˢ and Rᵗ are as defined above;

o) —CN;

p) —(C═O)H or —CH(OCH₃)₂;

q) —C(OCH₃)₂C₁₋₄ alkyl, where the alkyl is optionally mono-substituted by Rᑫ as defined above;

r) —(C═O)Rˢ, where Rˢ is as defined above;

s) —(C═NORᶻ)Rʸ where Rʸ and Rᶻ are as defined above, except they may not be joined together to form a ring;

t) —(C═O)OC₁₋₄ alkyl, where the alkyl is optionally mono-substituted by Rᑫ as defined above;

u) —(C═O)N(Rʸ)Rᶻ where Rʸ and Rᶻ are as defined above;

v) —(C═O)—N(ORʸ)Rᶻ where Rʸ and Rᶻ are as defined above, except they may not be joined together to form a ring;

w) —(C═S)N(Rʸ)(Rᶻ) where Rʸ and Rᶻ are as defined above;

x) —COOMᵇ, where Mᵇ is as defined above;

y) —SCN;

z) —SCF₃;

aa) tetrazolyl, where the point of attachment is the carbon atom of the tetrazole ring and one of the nitrogen atoms is mono-substituted by hydrogen, an alkali metal or a $C_1$-$C_4$ alkyl optionally substituted by $R^q$ as defined above;

ab) an anionic function selected from the group consisting of: phosphono [P=O(OM$^b$)$_2$]; alkylphosphono {P=O(OM$^b$)—[O($C_1$-$C_4$ alkyl)]}; alkylphosphinyl [P=O(OM$^b$)—($C_1$-$C_4$ alkyl)]; phosphoramido [P=O(OM$^b$)N(R$^y$)R$^z$ and P=O-(OM$^b$)NHR$^x$]; sulfino (SO$_2$M$^b$); sulfo (SO$_3$M$^b$); acylsulfonamides selected from the structures CONM$^b$SO$_2$R$^x$, CONM$^b$SO$_2$N(R$^y$)R$^z$, SO$_2$NM$^b$CON(R$^y$)R$^z$; and SO$_2$NM$^b$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by R$^q$, as defined above; M$^b$ is as defined above; and R$^y$ and R$^z$ are as defined above;

ac) $C_5$-$C_7$ cycloalkyl group in which one of the carbon atoms in the ring is replaced by a heteroatom selected from O, S, NH or N($C_1$-$C_4$ alkyl) and in which one additional carbon atom may be replaced by NH or N($C_1$-$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2$-$C_4$ alkenyl radical, optionally mono-substituted by one of the substituents a) to ac) above and phenyl which is optionally substituted by R$^q$ as defined above;

ae) $C_2$-$C_4$ alkynyl radical, optionally mono-substituted by one of the substituents a) to ac) above;

af) $C_1$-$C_4$ alkyl radical;

ag) $C_1$-$C_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from —S— and NR$^t$ (where R$^t$ is as defined above) and one of the saturated carbon atoms of the oxazolidinone ring is optionally mono-substituted by one of the substituents a) to ag) above; and M is selected from:
i) hydrogen;
ii) a pharmaceutically acceptable esterifying group or removable carboxyl protecting group;
iii) an alkali metal or other pharmaceutically acceptable cation; or
iv) absent, leaving COO— with the proviso that when M is as described in i), ii) or iii), a negatively counterion is present.

2. The compound of claim 1 wherein $R^1$ is hydrogen and $R^2$ is (R)—CH$_3$CH(OH)— or (R)—CH$_3$CH(F)—.

3. The compound of claim 2 wherein at least $R^a$ in the 5′-position of said N-pyridiniumphenyl is other than hydrogen.

4. The compound of claim 2 wherein up to two $R^a$ substituents are other than hydrogen.

5. A compound according to claim 2 wherein at least one $R^a$ is other than hydrogen and is selected from the group consisting of:

| | |
|---|---|
| —OCH$_3$ | —OCH$_2$CO$_2$CH$_3$ |
| —OCH$_2$CH$_2$OH | —CF$_3$ |
| —F | —Cl |
| —Br | —I |
| —OH | —OCOCH$_3$ |
| —OCONH$_2$ | —SCH$_3$ |
| —SOCH$_3$ | —SO$_2$CH$_3$ |
| —SCH$_2$CH$_2$OH | —SOCH$_2$CH$_2$OH |
| —SO$_2$NH$_2$ | —SO$_2$N(CH$_3$)$_2$ |
| —NHCHO | —NHCOCH$_3$ |
| —NHCO$_2$CH$_3$ | —NHSO$_2$CH$_3$ |
| —CN | —CHO |
| —COCH$_3$ | —COCH$_2$OH |
| —CH=NOH | —CH=NOCH$_3$ |
| —CH=NOCH$_2$CO$_2$CH$_3$ | —CH=NOCMe$_2$CONH$_2$ |
| —CH=NOCMe$_2$CO$_2$Me | —CO$_2$CH$_2$CH$_2$OH |
| —CONH$_2$ | —CONHCH$_3$ |
| —CON(CH$_3$)$_2$ | —CONHCH$_2$CN |
| —CONHCH$_2$CONH$_2$ | —CONHCH$_2$CO$_2$CH$_3$ |
| —CONHOH | —CONHOCH$_3$ |
| -tetrazolyl | —CO$_2$CH$_3$ |
| —SCF$_3$ | —CONHSO$_2$Ph |
| —CONHSO$_2$NH$_2$ | —SO$_2$CF$_3$ |
| —SO$_2$NHCN | —SO$_2$NHCONH$_2$ |
| —CH=CHCN | —CH=CHCONH$_2$ |
| —CH=CHCO$_2$CH$_3$ | —C≡C—CONH$_2$ |
| —C≡C—CN | —CH$_2$OH |
| —CH$_2$N$_3$ | —CH$_2$CO$_2$CH$_3$ |
| —SO$_2$CH$_2$CH$_2$OH | —CH$_2$I and |
| —SCH$_2$CONH$_2$. | |

6. A compound of the formula:

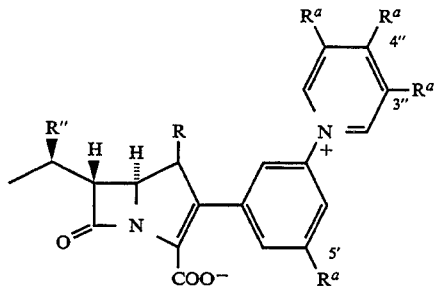

where R″ is F or OH, R is H or Me and R$^a$ is:

| # | R$^a$ | R$^a$ position |
|---|---|---|
| 1 | —H | — |
| 2 | —OCH$_3$ | 5′ |
| 3 | —OCH$_2$CO$_2$CH$_3$ | 5′ |
| 4 | —OCH$_2$CH$_2$OH | 5′ |
| 5 | —CF$_3$ | 5′ |
| 6 | —F | 5′ |
| 7 | —Cl | 5′ |
| 8 | —Br | 5′ |
| 9 | —I | 5′ |
| 10 | —OH | 5′ |
| 11 | —OCOCH$_3$ | 5′ |
| 12 | —OCONH$_2$ | 5′ |
| 13 | —SCH$_3$ | 5′ |
| 14 | —SOCH$_3$ | 5′ |
| 15 | —SO$_2$CH$_3$ | 5′ |
| 16 | —SCH$_2$CH$_2$OH | 5′ |
| 17 | —SOCH$_2$CH$_2$OH | 5′ |
| 18 | —SCH$_2$CONH$_2$ | 5′ |
| 19 | —SO$_2$NH$_2$ | 5′ |
| 20 | —SO$_2$N(CH$_3$)$_2$ | 5′ |
| 21 | —NHCHO | 5′ |
| 22 | —NHCOCH$_3$ | 5′ |
| 23 | —NHCO$_2$CH$_3$ | 5′ |

-continued

| # | $R^a$ | $R^a$ position |
|---|---|---|
| 24 | —NHSO₂CH₃ | 5' |
| 25 | —CN | 5' |
| 26 | —CHO | 5' |
| 27 | —COCH₃ | 5' |
| 28 | —COCH₂OH | 5' |
| 29 | —CH=NOH | 5' |
| 30 | —CH=NOCH₃ | 5' |
| 31 | —CH=NOCH₂CO₂CH₃ | 5' |
| 32 | —CH=NOCMe₂CO₂CH₃ | 5' |
| 33 | —CH=NOCMe₂CONH₂ | 5' |
| 34 | —CO₂CH₂CH₂OH | 5' |
| 35 | —CONH₂ | 5' |
| 36 | —CONHCH₃ | 5' |
| 37 | —CON(CH₃)₂ | 5' |
| 38 | —CONHCH₂CN | 5' |
| 39 | —CONHCH₂CONH₂ | 5' |
| 40 | —CONHCH₂CO₂CH₃ | 5' |
| 41 | —CONHOH | 5' |
| 42 | —CONHOCH₃ | 5' |
| 43 | -tetrazolyl | 5' |
| 44 | —CO₂CH₃ | 5' |
| 45 | —SCF | 5' |
| 46 | —CONHSO₂Ph | 5' |
| 47 | —CONHSO₂NH₂ | 5' |
| 48 | —SO₂CF₃ | 5' |
| 49 | —SO₂NHCN | 5' |
| 50 | —SO₂NHCONH₂ | 5' |
| 51 | —CH=CHCN | 5' |
| 52 | —CH=CHCONH₂ | 5' |
| 53 | —CH=CHCO₂CH₃ | 5' |
| 54 | —C≡C—CONH₂ | 5' |
| 55 | —C≡C—CN | 5' |
| 56 | —CH₂OH | 5' |
| 57 | —CH₂N₃ | 5' |
| 58 | —CH₂CO₂CH₃ | 5' |
| 59 | —SO₂CH₂CH₂OH | 5' |
| 60 | —CH₂I | 5' |
| 61 | —CONH₂ | 3" |
| 62 | —CONH₂ | 4" |
| 63 | —CN | 3" |
| 64 | —CN | 4" |
| 65 | —CHO | 3" |
| 66 | —CHO | 4" |
| 67 | —CH₂OH | 3" |
| 68 | —CH₂OH | 4" |
| 69 | —Br | 3" |
| 70 | —Br | 4" |
| 71 | —I | 3" |
| 72 | —I | 4" |
| 73 | —SO₂CH₃ | 3" |
| 74 | —SO₂CH₃ | 4" |
| 75 | —S(O)CH₃ | 3" |
| 76 | —S(O)CH₃ | 4" |
| 77 | —SCH₃ | 3" |
| 78 | —SCH₃ | 4" |
| 79 | —COOCH₃ | 3" |
| 80 | —COOCH₃ | 4" |
| 81 | —CH=NOH | 3" |
| 82 | —CH=NOH | 4" |

7. A compound of the formula:

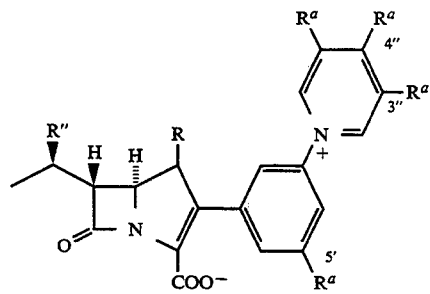

where R" is F or OH, R is H or Me and $R^a$ is:

| # | $R^a$ | |
|---|---|---|
| 1 | 3"-CH₂OH | 5'-Br |
| 2 | 4"-CH₂OH | 5'-Br |
| 3 | 3"-CH₂OH | 5'-CN |
| 4 | 4"-CH₂OH | 5'-CN |
| 5 | 3"-CH₂OH | 5'-S(O)₂Me |
| 6 | 4"-CH₂OH | 5'-S(O)₂Me |
| 7 | 3"-CH₂OH | 5'-I |
| 8 | 4"-CH₂OH | 5'-I |
| 9 | 3"-CHO | 5'-Br |
| 10 | 4"-CHO | 5'-Br |
| 11 | 3"-CHO | 5'-CN |
| 12 | 4"-CHO | 5'-CN |
| 13 | 3"-CHO | 5'-S(O)₂Me |
| 14 | 4"-CHO | 5'-S(O)₂Me |
| 15 | 3"-CHO | 5'-I |
| 16 | 4"-CHO | 5'-I |

8. A composition comprising a pharmaceutically acceptable carrier and from 0.1% to about 99% by weight of active material of claim 1.

9. A composition according to claim 8 which further comprises an inhibitorily effective amount of a DHP inhibitor.

10. A composition according to claim 9 wherein said DHP inhibitor is 7-(L-2-amino-2-carboxyethylthio)-2-(2,2-dimethylcyclopropanecarboxamide)-2-heptanoic acid.

11. A method for treating bacterial infection in mammals comprising administering a pharmaceutical composition comprising an effective amount of a compound of claim 1 and a pharmaceutically acceptable carrier therefor to said mammals.

12. A method according to claim 11 which further comprises administering an inhibitorily effective amount of a DHP inhibitor.

13. A method according to claim 12 wherein said DHP inhibitor is 7-(L-2-amino-2-carboxyethylthio)-2-(2,2-dimethylcyclopropanecarboxamide )-2-heptanoic acid.

14. A compound selected from the group consisting of:

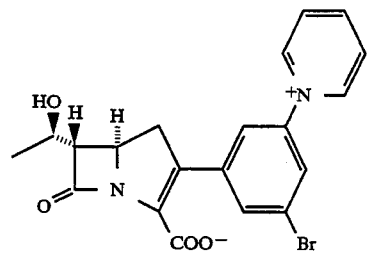

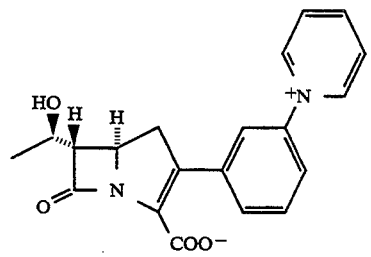

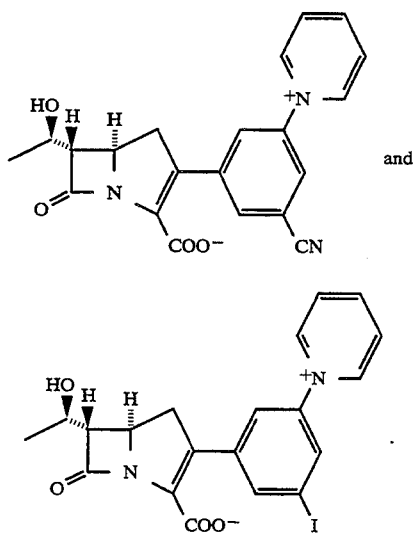

and

15. A compound of the formula:

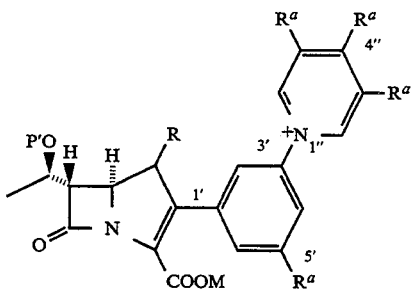

wherein:

R is H or CH$_3$;

R$^a$ are independently selected from the group consisting of hydrogen and the radicals set out below and —SnMe$_3$:

a) —CF$_3$;

b) a halogen atom selected from the group consisting of: —Br, —Cl, —F, or —I;

c) —OC$_{1-4}$ alkyl, wherein the alkyl is optionally mono-substituted by R$^q$, where R$^q$ is a member selected from the group consisting of —OP′, —OH, —OCH$_3$, —CN, —C(O)NH$_2$, —OC(O)NH$_2$, CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$ (where M$^a$ is M, hydrogen, alkali metal, methyl or phenyl), tetrazolyl (where the point of attachment is the carbon atom of the tetrazole ring and one of the nitrogen atoms is mono-substituted by M$^a$ as defined above) and —SO$_3$M$^b$ (where M$^b$ is M, hydrogen or an alkali metal);

d) —OH and OP′;

e) —O(C=O)R$^s$, where

R$^s$ is C$_{1-4}$ alkyl or phenyl, each of which is optionally mono-substituted by R$^q$ as defined above or tri-substituted with —F;

f) —O(C=O)N(R$^y$)R$^z$ where

R$^y$ and R$^z$ are independently H, C$_{1-4}$ alkyl (optionally mono-substituted by R$^q$ as defined above), together a 3- to 5-membered alkylidene radical to form a ring (optionally substituted with R$^q$ as defined above) or together a 2- to 4-membered alkylidene radical, interrupted by —O—, —S—, —S(O)— or —S(O)$_2$— to form a ring (where the ring is optionally mono-substituted with Rq as defined above);

g) —S(O)$_n$—R$^s$ where n=0-2, and R$^s$ is defined above;

h) —SO$_2$N(R$^y$)R$^z$ where R$^y$ and R$^z$ are as defined above;

i) N$_3$ j) —N(R$^t$)(C=O)H, where

R$^t$ is is H or C$_{1-4}$ alkyl, and the alkyl thereof is optionally mono-substituted by R$^q$ as defined above;

k) —N(R$^t$)(C=O)C$_{1-4}$ alkyl, where R$^t$ is as defined above, and the alkyl group is optionally mono-substituted by R$^q$ as defined above;

l) —N(R$^t$)(C=O)OC$_{1-4}$ alkyl, where R$^t$ is as defined above, and the alkyl group is also optionally mono-substituted by R$^q$ as defined above:

m) —N(R$^t$)(C=O)N(R$^y$)R$^z$ where R$^t$, R$^y$ and R$^z$ are as defined above;

n) —N(R$^t$)SO$_2$R$^s$, where R$^s$ and R$^t$ are as defined above:

o) —CN;

p) —(C=O)H or —CH(OCH$_3$)$_2$;

q) —C(OCH$_3$)$_2$C$_{1-4}$ alkyl, where the alkyl is optionally mono-substituted by R$^q$ as defined above;

r) —(C=O)R$^s$, where R$^s$ is as defined above;

s) —(C=NOR$^z$)R$^y$ where R$^y$ and R$^z$ are as defined above, except they may not be joined together to form a ring;

t) —(C=O)OC$_{1-4}$ alkyl, where the alkyl is optionally mono-substituted by R$^q$ as defined above;

u) —(C=O)N(R$^y$)R$^z$ where R$^y$ and R$^z$ are as defined above;

v) —(C=O)—N(OR$^y$)R$^z$ where R$^y$ and R$^z$ are as defined above, except they may not be joined together to form a ring;

w) —(CS)N(R$^y$)(R$^z$) where R$^y$ and R$^z$ are as defined above;

x) —COOM$^b$, where M$^b$ is as defined above;

y) —SCN;

z) —SCF$_3$;

aa) tetrazolyl, where the point of attachment is the carbon atom of the tetrazole ring and one of the nitrogen atoms is mono-substituted by hydrogen, an alkali metal or a C$_1$-C$_4$ alkyl optionally substituted by R$^q$ as defined above;

ab) an anionic function selected from the group consisting of: phosphono [P=O(OM$^b$)$_2$]; alkylphosphono {P=O(OM$^b$)—[O(C$_1$-C$_4$ alkyl)]}; alkylphosphono {P=O(OM$^b$)—[O(C$_1$-C$_4$ alkyl)]}; alkylphosphinyl [P=O(OM$^b$)—(C$_1$-C$_4$ alkyl)]; phosphoramido [P=O(OM$^b$)N(R$^y$)R$^z$ and P=O(OM$^b$)NHR$^x$]; sulfino (SO$_2$M$^b$); sulfo (SO$_3$M$^b$); acylsulfonamides selected from the structures CONM$^b$SO$_2$R$^x$, CONM$^b$SO$_2$N-(R$^y$)R$^z$, SO$_2$NM$^b$CON(R$^y$)R$^z$; and SO$_2$NM$^b$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;

ac) $C_5$–$C_7$ cycloalkyl group in which one of the carbon atoms in the ring is replaced by a heteroatom selected from O, S, NH or N($C_1$–$C_4$ alkyl) and in which one additional carbon atom may be replaced by NH or N($C_1$–$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2$–$C_4$ alkenyl radical, optionally mono-substituted by one of the substituents a) to ac) above and phenyl which is optionally substituted by $R^q$ as defined above;

ae) $C_2$–$C_4$ alkynyl radical, optionally mono-substituted by one of the substituents a) to ac) above;

af) $C_1$–$C_4$ alkyl radical;

ag) $C_1$–$C_4$ alkyl mono-substituted by one of the substituents a)–ac) above;

ah) a 2-oxazolidinonyl moiety in which the point of attachment is the nitrogen atom of the oxazolidinone ring, the ring oxygen atom is optionally replaced by a heteroatom selected from —S— and $NR^t$ (where $R^t$ is as defined above) and one of the saturated carbon atoms of the oxazolidinone ring is optionally mono-substituted by one of the substituents a) to ag) above;

$\delta^-$ is

P' is a removable protecting group for hydroxy or hydrogen; and

M is a removable protecting group for carboxy.

16. The compound of claim 15 wherein P' is selected from the group consisting of hydrogen, t-butylmethoxyphenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl.

17. The compound of claim 15 wherein M is selected from the group consisting of benzhydryl, p-nitrobenzyl, 2-naphthylmethyl, allyl, 2-chloroallyl, benzyl, t-butyl, 2,2,2-trichloroethyl, t-butyldimethylsilyl, t-butyldiphenylsilyl, trimethylsilyl, 2-(trimethyl)silylethyl, phenacyl, p-methoxybenzyl, acetonyl, o-nitrobenzyl and 4-pyridylmethyl.

* * * * *

UNITED STATES PATENT AND TRADEMARK OFFICE
CERTIFICATE OF CORRECTION

PATENT NO.   : 5,382,575
DATED        : January 17, 1995
INVENTOR(S)  : Alan D. Adams, et al It is certified that error appears in the above-indentified patent and that said Letters Patent is hereby corrected as shown below:

In Claim 1, at column 26, line 5, replace "-SO$_2$, NH$_2$", with -- -SO$_2$NH$_2$ --.

In Claim 15, at column 31, line 25, replace the present structure with the following:

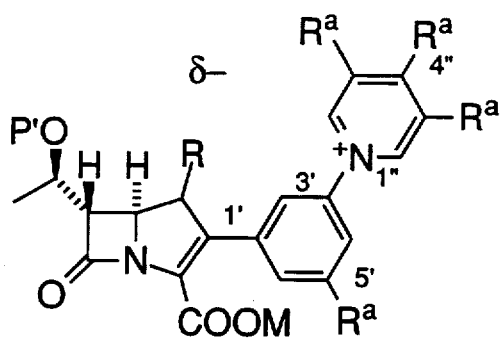

In Claim 15, column 32, line 40, replace " -(CS)N(R$^y$)(R$^z$) ", with -- -(C=S)N(R$^y$)(R$^z$) --.

In Claim 15, column 32, line 53, replace "alkylphosphono" with -- alkylphosphinyl -- .

Signed and Sealed this

Eighteenth Day of April, 1995

Attest:

BRUCE LEHMAN

Attesting Officer

Commissioner of Patents and Trademarks